United States Patent [19]

Cantrell, Jr. et al.

[11] Patent Number: 4,649,750

[45] Date of Patent: Mar. 17, 1987

[54] ACOUSTIC RADIATION STRESS MEASUREMENT

[75] Inventors: John H. Cantrell, Jr.; William T. Yost, both of Newport News, Va.

[73] Assignee: The United States of America as represented by the Administrator of the National Aeronautics and Space Administration, Washington, D.C.

[21] Appl. No.: 775,989

[22] Filed: Sep. 13, 1985

[51] Int. Cl.⁴ ............................................. G01N 29/00
[52] U.S. Cl. ..................................... 73/599; 73/1 DV
[58] Field of Search .............. 73/597, 599, 1 DV, 602

[56] References Cited

U.S. PATENT DOCUMENTS

| 4,312,228 | 1/1982 | Wohltjen | 73/597 |
| 4,399,702 | 8/1983 | Suzuki | 73/597 |
| 4,452,082 | 6/1984 | Miwa | 73/599 |
| 4,471,657 | 9/1984 | Voris et al. | 73/597 |
| 4,522,071 | 6/1985 | Thompson | 73/597 |

OTHER PUBLICATIONS

R. T. Smith, "Stress-Induced Anisotropy in Solids the Acousto-Elastic Effect", *Ultrasonics,* pp. 135-147, Jul.-Sep. 1963.

*Primary Examiner*—Stephen A. Kreitman
*Attorney, Agent, or Firm*—George F. Helfrich; John R. Manning; Robert D. Marchant

[57] ABSTRACT

Ultrasonic radio frequency toneburst are launched into a sample of material tested. The amplitude of the tonebursts and the slope of the resulting static displacement pulses are measured. These measurement are used to calculate the nonlinearities of the material.

10 Claims, 1 Drawing Figure

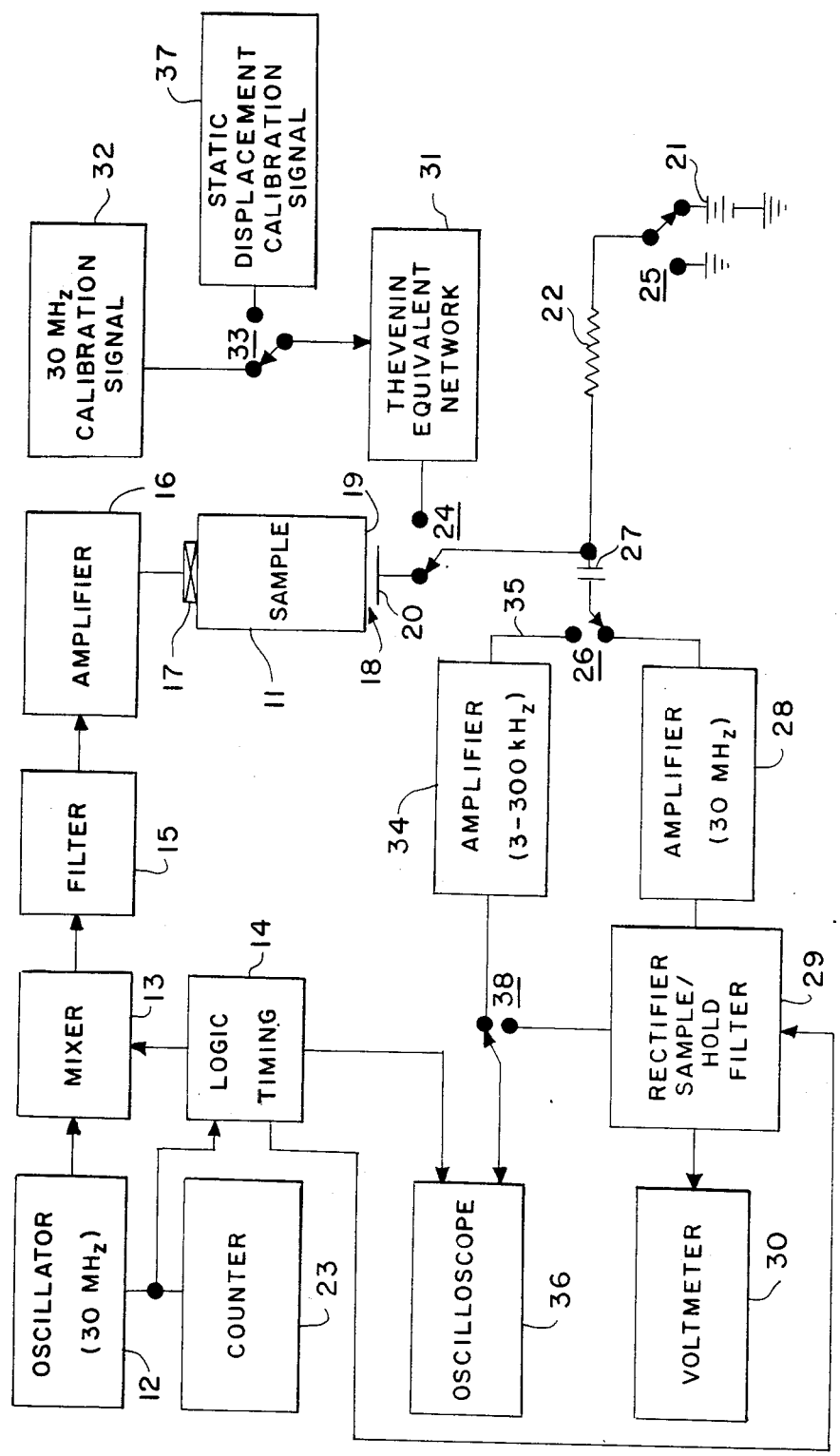

ACOUSTIC RADIATION STRESS MEASUREMENT

ORIGIN OF THE INVENTION

The invention herein was made by employees of the United States Government and may be manufactured and used by or for the Government for governmental purposes without the payment of any royalties thereon or therefor.

BACKGROUND OF THE INVENTION

The invention relates generally to acoustic radiation stress measurements and more specifically concerns a method and apparatus for quantitatively characterizing those properties of fluids and solids related to material nonlinearity.

Each material has a unique set of nonlinearity parameters that characterizes that material and which are related to the thermodynamic state of that material. The thermodynamic state is here generalized to include the degree of residual or applied stress, the atomic or molecular composition of the material, defect structures, and the state of material order or disorder. The nonlinearity parameter thus serves as an important and distinct measure of the material state that is both complementary and supplementary to acoustic velocity and acoustic attenuation measurements.

Operationally, the nonlinearity parameter is responsible for acoustic waveform distortion leading to acoustic harmonic generation (the harmonics of the fundamental driving frequency) and acoustic radiation-induced static strains in the material. The acoustic radiation induced static strains are a manifestation of the acoustic radiation stress in the material. The previous art has been to measure the nonlinearity parameters by means of a harmonic generation method. The harmonic generation method, however, is sensitive to phase cancellation artifacts in the transducer and cannot give unambiguous values for the sign of the nonlinearity parameters without the addition of a phase detection system which must be calibrated to a standard sample.

It is the primary object of this invention to provide a method and apparatus for measuring the nonlinear parameters of a material that characterize that material.

Another object of this invention is to provide a method and apparatus for quantitatively characterizing those properties of fluids and solids related to material nonlinearity without the addition of a phase detection system.

Other objects and advantages of this invention will become apparent hereinafter in the specification and drawing.

SUMMARY OF THE INVENTION

Ultrasonic radio frequency (rf) tonebursts are launched into a sample of the material tested. These tonebursts generate low frequency static displacement pulses having the shape of a right angled triangle. The amplitude of the tonebursts and the slope of the right angled triangle are measured and these measurements are used to calculate the acoustic nonlinear parameter of the material. The polarization of the toneburst can be varied to give a different acoustic nonlinear parameter for each polarization.

BRIEF DESCRIPTION OF THE DRAWING

The sole FIGURE is a drawing of the apparatus used to measure the amplitude of the toneburst and the slope of the static displacement pulse.

DETAILED DESCRIPTION OF THE INVENTION

Turning now to the drawing of the apparatus for illustrating the invention, the number 11 designates a sample of the material whose nonlinear parameters are to be measured. A 30-MHz rf signal from a continuous-wave oscillator 12 is combined in a mixer 13 with a gating pulse from a logic and timing generator 14. The logic and timing generator 14 counts down from the oscillator 12 reference to time the generation of the gating pulse to the mixer 13. The length of the gating pulse is set such that the resulting gated rf signal from mixer 13 is composed of an integral number of 30-MHz cycles. Such an arrangement assures phase coherence of each rf pulse. The gated rf pulse is fed through a 8.5-MHz high pass filter 15 to remove any leakage of the gating pulse through the mixer 13. The rf pulse is amplified by a 100-W broadband linear rf amplifier 16 and is used to drive a 30-MHz narrow-based lithium niobate transducer 17 bonded to one end of sample 11. The transducer 17 generates a gated 30-MHz ultrasonic signal or toneburst which propagates through the sample 11. The toneburst is received by a broadband air-gap capacitive transducer 18 at the opposite end of the sample.

The capacitive transducer 18 is a parallel plate arrangement in which the sample end surface 19 functions as the ground plate. The other plate 20 is an optically flat electrode which is recessed approximately 7 $\mu$m from the sample surface. A dc bias 21 of 50 V is applied through a 1-M ohm resistor 22 to plate 20. It is known that the measurement of the output voltage from such a capacitive arrangement may be converted to a displacement measurement of the sample surface using the relation $$V_d = V_b(u/s) \tag{1}$$

Where $V_d$ is the output voltage, $V_b$ is the dc bias voltage, u is the displacement of the sample surface, and s is the gap spacing between the capacitor plates 19 and 20. The capacitive transducer 18 is capable of measuring displacement amplitudes of the order of $10^{-4}$ Å.

The theory on which this invention is based is found in *Physical Review B*, Volume 30, Number 6, Sept. 15, 1984, pages 3221-3227. This theory predicts that an acoustic toneburst propagating through a solid generates a radiation-induced static pulse having the shape of a right-angled triangle. The slope of the triangular pulse is dependent upon the frequency and amplitude of the toneburst as well as the acoustic nonlinearity parameter of the solid. The theory can be stated mathematically as follows:

$$B_j = [-4m/(k^2(P_j)^2 C_o)] \tag{2}$$

Where $B_j$ is the nonlinear parameter, m is the slope of the radiation-induced static pulse, $P_j$ is the amplitude of the toneburst, $C_o$ is the small-amplitude sound wave velocity and k is the propagation number which is equal to $w/C_o$ where w is the frequency of oscillator 12 as indicated by a counter 23. The subscript j = 1,2,3 is the index of polarization of the acoustic wave corresponding to one quasilongitudinal and two quasitransverse modes. The polarization is introduced by transducer 17 as is well known in the art. The value for $P_j$ in equation (2) can be determined by measuring the amplitude $V_d$ of the rf output at plate 20 and solving equation (1) for u which corresponds to $P_j$. The remaining circuitry in the drawing is for measuring $V_d$ and the slope of the radiation induced static pulse.

The displacement amplitude of the rf toneburst is obtained by placing switches 24, 25, and 26 in the positions shown. Consequently, the output form transducer 18 is fed through a capacitor 27 into a 30 MHz amplifier 28. The output from the amplifier 28 is sent into a rectifier and filter assembly 29 which converts the 30-MHz toneburst into a detected signal. The rectifier and filter assembly also contains a sample and hold circuit which, when strobed, holds the voltage of the detected signal. The strobe signal is set by the logic and timing circuit 14 and is adjusted to coincide with the center of the first toneburst through the sample 11 following the electrical drive pulse to the transducer (i.e. the first ultrasonic echo). The output of the sample and hold is measured by a voltmeter 30 and recorded.

The capacitive transducer 18 is now switched out and a Thevenin equivalent network 31 is switched into the circuit by means of switch 24. The parameters of the Thevenin equivalent network 31 are set to match the appropriate values of the capacitive transducer 18. The resistor 22 is removed from the bias source 21 and that end grounded by means of switch 25 to prevent electrical surges through the circuits which may damage the instruments. A substitutional 30-MHz calibration signal 32 is now switched, by means of a switch 33, into the Thevenin equivalent network 31 and adjusted in amplitude until the Voltmeter 30 reads the same value as that of the ultrasonic toneburst measurement. Since the amplitude of the 30-MHz calibration signal 32 is measured at the input to the Thevenin equivalent network 31, the measured value is equal to the signal voltage produced by the capacitive transducer 18.

In order to display the acoustic-radiation-induced static displacement pulse the output of the capacitive transducer 18 is connected through switch 24 to a Princeton Applied Research Model-113 low frequency (3-300 kHz) amplifier 34 by switch 26 and a short, low capacitance lead 35. The narrow band width is necessary to reduce electrical noise in the measurement of the small static displacement signal. The output of the amplifier 34 is sent to an oscilloscope 36 where the static displacement signal is displayed. A template (not shown) is placed over the screen to record the static pulse shape.

The measurement of the slope of the static displacement pulse is performed by grounding resistor 22 by means of switch 25 and switching to the Thevenin equivalent network 31 by means of switch 24. A static displacement calibration signal 37 (Hewlett-Packard 3314A function generator) having the shape of a right-angled triangle is connected to the Thevenin equivalent network 31 by means of switch 33. The amplitude and width (reciprocal frequency) of the calibration signal is adjusted until the slope is identical to that of the acoustic-radiation-induced static displacement pulse. The slope of the static displacement pulse is readily obtained from the measured calibration signal and is expressed in units of displacement per unit of time using equation (1). Switch 38 is for connecting rectifier filter 29 to the oscilloscope 36 while the amplitude of the toneburst is being measured.

The advantage of this invention is that is can be used to characterize material nonlinearity in solids and liquids and uncover material properties not previously known. The invention is expected to become an important research tool in the understanding of material properties. With appropriate refinements the invention may serve as a field monitor for the NDE of material properties related to strength and residual/applied stresses.

In a stress free isotropic solid the shear wave nonlinearity parameter is zero. When the isotropic solid has applied or residual stresses the shear wave nonlinearity parameter becomes non-zero because of stress induced anisotropy. In such a case the value of the nonlinearity parameter becomes a measure of the stress field in a solid when compared to the stress free isotropic solid.

Alternative embodiments of the invention pertain primarily to the specific methods for detection of the acoustic signals. For example, rather than using a broadband capacitance transducer as was used in the prototype model, a calibrated point contact transducer having an appropriately large bandwidth extending to low frequencies may be employed or an optical transducer employing a phase hetrodyning scheme may be used.

For transparent media the Raman-Nath diffraction technique using coherent light impinging at right angles to the acoustic propagation direction may be employed. The essential feature of the detection system is that it must be capable of measuring absolute amplitudes of the acoustic signals for absolute measurement of the nonlinearity parameter. For applications such as acoustic imaging where only relative values of the nonlinearity parameters are of interest the absolute amplitude requirement may be relaxed.

What is claimed is:

1. A method for measuring the nonlinear characterizing parameters of a material comprising the steps of:
    providing a material to be analyzed;
    applying a gated rf ultrasonic signal to a sample of said material at several different polarizations;
    measuring the amplitude of said gated rf ultrasonic signal;
    measuring the slope of the static displacement pulse generated by said gated rf ultrasonic signal; and
    calculating the nonlinear characterizing parameter by using said measured amplitude and slope in the following equation:

$$Bj = [-4m/(k^2(P_j)^2 C_o]$$

where B is the nonlinear characterizing parameter; the j index represents the polarization of said gated rf ultrasonic signal; $k = w/C_o$, where w is the frequency of the gated rf ultrasonic signal; $C_o$ is the small-amplitude sound wave velocity; $P_j$ is the amplitude of the gated rf ultrasonic signal; and m is the slope of the static displacement pulse generated by said gated rf ultrasonic signal.

2. A method according to claim 1 wherein the step of measuring the amplitude of said rf ultrasonic signal comprises the steps of changing the rf ultrasonic signal to an rf electrical signal, rectifying the rf electrical signal, measuring the amplitude of the rectified signal, rectifying and measuring an rf calibration signal and changing the amplitude of the rf calibration signal until the two rectified signals are equal.

3. A method according to claim 1 wherein the step of measuring the slope of the static displacement pulse comprises the steps of producing a picture of the slope of the static displacement pulse, producing a picture of a static displacement calibration signal and varying the slope of the static displacement calibration signal until the two pictures coincide.

4. A method according to claim 1 including the further step of comparing the amplitude and slope measurements of the material with a stress free isotropic solid whose shear wave nonlinearity parameter is zero to measure the stress field in the solid being tested.

5. Apparatus for measuring the nonlinear characterizing parameters of a material comprising:
   means for generating a gated rf signal;
   first transducer means for applying said gated rf signal to a sample of said material at several different polarizations to produce gated rf ultrasonic signals in said sample;
   second transducer means for receiving said gated rf ultrasonic signal and converting it to an output signal;
   means for measuring the amplitude of said output signal;
   means for measuring the slope of said output signal;
   means for calculating said nonlinear characterizing parameter by using the following equation:

$$Bj = [-4m/(k^2(P_j)^2 C_o)]$$

where B is the nonlinear characterizing parameter; the j index represents the polarization of said gated rf ultrasonic signal; $k = w/C_o$, where w is the frequency of the gated rf ultrasonic signal; $C_o$ is the small-amplitude sound wave velocity; $P_j$ is the amplitude of the gated rf ultrasonic signal; and m is the slope of the static displacement pulse generated by said gated rf ultrasonic signal.

6. Apparatus according to claim 5 wherein said second transducer is a broadband air-gap capacitive transducer.

7. Apparatus according to claim 6 wherein said means for measuring the rf amplitude of said output signal comprises an rf calibration signal that is adjustable in amplitude connected to a Thevenin equivalent network, a switch means for selecting the output from said second transducer or the output from said Thevenin equivalent network and means for measuring the rf amplitude at the output of said switch means whereby the rf amplitude of said output signal can be measured by comparing it with the rf calibration signal.

8. Apparatus according to claim 7 wherein said means for measuring the rf amplitude at the output of said switch means includes an rf amplifier, a rectifier filter and a voltmeter.

9. Apparatus according to claim 6 wherein said means for measuring the low frequency slope of said output signal comprises a right angled function generator with its output applied to a Thevenin equivalent network, switch means for selecting the output from said second transducer or the output from said Thevenin equivalent network and means for measuring the low frequency slope at the output of said switch means whereby the low frequency slope at the output of said second transducer can be measured by comparing it with the known slope of the output of the right angled function generator.

10. Apparatus according to claim 9 wherein said means for measuring the low frequency slope at the output of said switch means includes a low frequency amplifier and an oscilloscope.

* * * * *